United States Patent [19]
Exner et al.

[11] Patent Number: 5,811,574
[45] Date of Patent: Sep. 22, 1998

[54] CONTINUOUS PREPARATION OF ALKYL ESTERS OF (METH)ACRYLIC ACID AND APPARATUS FOR THIS PURPOSE

[75] Inventors: Herbert Exner, Waldsee; Karl Baur, Ludwigshafen; Toni Dockner, Meckenheim; Christiane Potthoff, Dortmund; Albrecht Dams, Wachenheim, all of Germany

[73] Assignee: BASF Aktiengesellschaft, Ludwigshafen, Germany

[21] Appl. No.: 713,208

[22] Filed: Sep. 12, 1996

[30] Foreign Application Priority Data

Sep. 28, 1995 [DE] Germany .......... 195 36 178.4

[51] Int. Cl.⁶ .................................................. C07C 69/52
[52] U.S. Cl. ............................................................. 560/205
[58] Field of Search ............................................. 560/205

[56] References Cited

FOREIGN PATENT DOCUMENTS

| 0 733 617 | 9/1996 | European Pat. Off. . |
| 14 68 932 | 12/1968 | Germany . |
| 2 226 829 | 12/1973 | Germany . |
| 2 252 334 | 5/1974 | Germany . |
| 25 52 987 | 6/1977 | Germany . |
| 3146191 | 5/1983 | Germany . |
| 33 08 879 | 9/1983 | Germany . |
| 770551 | 3/1957 | United Kingdom . |
| 1017522 | 1/1966 | United Kingdom . |

*Primary Examiner*—Paul J. Killos
*Attorney, Agent, or Firm*—Oblon, Spivak, McClelland, Maier & Neustadt, P.C.

[57] ABSTRACT

In a process and an apparatus for the continuous preparation of alkyl esters of (meth)acrylic acid by reacting (meth) acrylic acid and monohydric alkanols of 1 to 8 carbon atoms in the homogeneous, liquid, solvent-free phase at elevated temperatures and in the presence of an acidic esterification catalyst, by feeding the (meth)acrylic acid, the alkanol and the acid catalyst continuously to a reaction zone, the reaction zone consists of a cascade of at least two reaction regions connected in series, and the discharge stream of one reaction region forms a feed stream of a downstream reaction region. The cascade may have from two to four reaction regions spatially separated from one another.

16 Claims, 2 Drawing Sheets

CONTINUOUS PREPARATION OF ALKYL ESTERS OF (METH)ACRYLIC ACID AND APPARATUS FOR THIS PURPOSE

The present invention relates to a process for the continuous preparation of alkyl esters of (meth)acrylic acid by reacting (meth)acrylic acid and a monohydric alkanol of 1 to 8 carbon atoms in the homogeneous, liquid, solvent-free phase at elevated temperatures and in the presence of an acidic esterification catalyst, in which the (meth)acrylic acid, the alkanol and the acid catalyst are fed continuously to a reaction zone, the alkyl (meth)acrylate formed is separated off by rectification, after a residence time, via the top of a rectification zone mounted on the reaction zone, as a component of at least one azeotropic mixture consisting of water or water and starting alkanol as further components in addition to the alkyl (meth)acrylate, the resulting distillate is separated into at least one organic phase containing the alkyl (meth)acrylate and into at least one water-containing aqueous phase, a part of the organic phase containing aryl (meth)acrylate is recycled via the top of the rectification zone and, if required, water is recycled to the reaction zone, the alkyl (meth)acrylate is isolated from the excess organic phase containing the alkyl (meth)acrylate and a part of the reaction mixture is discharged continuously from the reaction zone.

The term (meth)acrylic acid denotes, in a known manner, acrylic or methacrylic acid. Alkyl esters of (meth)acrylic acid are generally known and are important, for example, as starting monomers for the preparation of aqueous polymer dispersions, which are used, for example, as adhesives.

Processes for the preparation of alkyl (meth)acrylates by reacting (meth)acrylic acid with monohydric alkanols of 1 to 8 carbon atoms in the homogeneous liquid phase at elevated temperatures and in the presence of proton-donating catalysts are known and are described, for example, in DE-A 14 68 932, 22 26 829 and 22 52 334. These are typical equilibrium reactions in which the conversion of the (meth) acrylic acid and of the particular alkanol to the corresponding ester is significantly limited by the equilibrium constant. Consequently, for an economical procedure, the unconverted starting materials have to be separated from the resulting ester and recycled to the reaction zone. As a rule, separating the resulting ester from unconverted (meth) acrylic acid proves to be particularly difficult since their boiling points are generally comparatively close together. Various measures for increasing the conversion of the (meth) acrylic acid to the corresponding esters have therefore been proposed, for example the use of an increased molar excess of alkanol relative to the (meth)acrylic acid, and the removal of the water of reaction by means of an organic entraining agent which forms a suitable azeotropic mixture or the extraction of the resulting ester with a suitable solvent during the reaction. However, these methods have the disadvantage that a large excess of alkanol must be recovered or the entraining agent or the extracting agent must be isolated. In addition, a large excess of alkanol promotes the formation of its dialkyl ether as a byproduct.

It is now also known that the difference between the boiling point of unconverted (meth)acrylic acid and that of resulting alkyl ester can be increased by incorporating the resulting alkyl ester of (meth)acrylic acid in at least one low-boiling aqueous azeotropic mixture which may also contain starting alkanol in addition to the alkyl (meth) acrylate and water, and by removing the alkyl (meth)acrylate continuously by rectification, as a component of at least one such azeotropic mixture, from the reaction zone comprising the unconverted (meth)acrylic acid, and thus separating it from unconverted (meth)acrylic acid. When the above procedure is carried out continuously, the aqueous azeotropic mixture obtained as the distillate is separated into at least one organic phase containing the alkyl (meth)acrylate and into at least one water-containing aqueous phase. A part of the organic phase containing the alkyl (meth)acrylate is recycled via the top of the attached rectification zone in order to establish the rectificative separation effect (rectificative reflux ratio).

If the aqueous azeotropic mixture which contains the desired ester and is separated off continuously from the reaction zone via the top of a rectification zone in the course of the novel process is not a hetero azeotropic mixture, said azeotropic mixture does not separate spontaneously into an aqueous phase and an organic phase after its condensation. However, this separation can be achieved in a simple manner, for example by extracting the alkanol contained in the azeotropic mixture by means of water and separating the resulting water/alkanol mixture by rectification. The alkanol is advantageously recycled to the reaction zone, preferably via the top of the attached rectification zone in order to establish the rectificative separation effect.

The alkyl (meth)acrylate is separated in a manner known per se from the excess organic phase containing the alkyl (meth)acrylate. In the esterification of lower $C_1$-and $C_2$ alkanols, the water of reaction formed as a byproduct in the course of the esterification is usually sufficient for forming the composition of the aqueous azeotropic mixture (suitable compositions of aqueous azeotropic mixtures are described, for example, in Azeotropic Data-III, Advances in Chemistry, Series 116, American Chemical Society, Washington, D.C. (1973)) and is thus removed simultaneously and continuously from the esterification equilibrium as a component of the aqueous azeotropic mixture. However, this is no longer so with increasing chain length of the alkanol, and in these cases additional water over and above the water of reaction formed in the course of the esterification must be introduced into the reaction zone. This is realized in the simplest manner by recycling to the esterification part an appropriate portion of the aqueous phase produced during separation of the aqueous azeotropic mixture obtained as the distillate. Since water tends to have an adverse effect with regard to the conversion in the actual esterification reaction, the recycling of the aqueous phase is preferably effected via the top of the attached rectification zone. If the aqueous azeotropic mixture separated off by rectification via the top of the attached rectification zone contains starting alkanol as an additional component, this is separated in a manner known per se from the excess of organic and aqueous phase remaining after separation of the azeotropic distillate into an organic and an aqueous phase after its partial recycling, and is recycled to the reaction zone. Since the starting alkanol, as one of the two reactants, participates directly in the esterification, this recycling is advantageously effected preferably by a direct route.

GB-1017522 discloses an appropriate process for the preparation of n-butyl acrylate. As esterification conditions, GB-1017522 recommends a molar ratio of starting alkanol to starting acid of from 2.3 to 5, a reaction temperature of <100° C. and a content of catalytically active sulfuric acid or organic sulfonic acid of from >0.05 to <5% by weight, based on the total mass of the reactants. The disadvantage of this procedure is the required large excess of starting alkanol, which promotes the formation of undesirable dialkyl ether, and the fact that the yield of n-butyl acrylate, based on the amount of acrylic acid used, is not completely satisfactory under the abovementioned conditions.

German Patent 2,552,987 discloses a process for the continuous preparation of alkyl esters of acrylic acid by reacting acrylic acid and a monohydric alkanol of 1 to 4 carbon atoms in the homogeneous, liquid, solvent-free phase in a molar ratio of from 1 (alkanol):1 (acrylic acid) to 2 (alkanol):1 (acrylic acid) at elevated temperatures and in the presence of sulfuric acid or an organic sulfonic acid as a catalyst, in which the acrylic acid, the alkanol and the acid catalyst are fed continuously to a reaction zone, the resulting alkyl acrylate is separated by rectification, after a residence time of a few hours, as a component of at least one aqueous azeotropic mixture consisting of water or water and starting alkanol as further components in addition to the alkyl acrylate, via the top of a rectification column mounted on the reaction zone and having a top pressure of from 0.1 to 1 atm, the resulting distillate I is separated into an organic phase containing the resulting acrylate and into an aqueous phase, a part of the organic phase is recycled via the top of the rectification zone in order to produce a greater separation effect and, if required, a part of the aqueous phase is recycled via the top of the rectification zone in order to maintain the composition of the aqueous azeotropic mixture, the alkyl ester is isolated in a manner known per se from the excess organic phase and a part of the reaction mixture is discharged from the reaction zone and is freed from high boilers by distillation and the resulting distillate II is recycled to the reaction zone.

The primary object of German Patent 2,552,987 is to avoid undesirable ether formation from a starting alkanol. However, the disadvantage of the procedure of German Patent 2,552,987 is that, in spite of the distillative treatment of the discharge from the reaction mixture and recycling of the resulting distillate to the reaction zone, the yield of alkyl acrylate, based on acrylic acid used, is unsatisfactory. The achieved reduction in the formation of the dialkyl ether byproduct is also not completely satisfactory. Furthermore, the residence time required in the Examples is unsatisfactory. This also applies to the space-time yield. It is assumed that this is due to the low concentration of acidic esterification catalyst.

It has therefore been proposed (German Patent Application 195 10 891.4) to carry out the corresponding esterification process in the presence of high concentrations of acidic esterification catalyst, which promotes the recleavage of oxyesters formed in the esterification of further byproducts and hence, for a given residence time, increases the yield of ester, based on (meth)acrylic acid used.

It is an object of the present invention to provide an esterification process for the preparation of alkyl esters of (meth)acrylic acid which permits an optimized yield of ester and at the same time a minimization of the formation of dialkyl ether byproduct.

We have found that this object is achieved by a process for the continuous preparation of alkyl esters of (meth) acrylic acid by reacting (meth)acrylic acid and a monohydric alkanol of 1 to 8 carbon atoms in the homogeneous, liquid, solvent-free phase at elevated temperatures and in the presence of an acidic esterification catalyst, in which the (meth) acrylic acid, the alkanol and the acid catalyst are fed continuously to a reaction zone, the alkyl (meth)acrylate formed is separated off by rectification, after a residence time, via the top of a rectification zone mounted on the reaction zone, as a component of at least one azeotropic mixture consisting of water or water and starting alkanol as further components in addition to the alkyl (meth)acrylate, the resulting distillate is separated into at least one organic phase containing the alkyl (meth)acrylate and into at least one water-containing aqueous phase, a part of the organic phase containing alkyl (meth)acrylate is recycled via the top of the rectification zone and, if required, water is recycled to the reaction zone, the alkyl (meth)acrylate is isolated from the excess organic phase containing the alkyl (meth)acrylate and a part of the reaction mixture is discharged continuously from the reaction zone, wherein the reaction zone consists of a cascade of at least two, preferably continuously operated, reaction regions, connected in series, and the liquid discharge stream of one reaction region forms the feed stream of the subsequent reaction region.

In this process, the amount by weight, based on the amount of esterification mixture contained in the particular reaction region, of acidic esterification catalyst increases along the reaction cascade owing to the relatively poor volatility of the acidic esterification catalyst. This leads to a spatial separation of esterification and recleavage and gives rise to reduced dialkyl ether formation. However, this acid profile may also be achieved along the cascade by external addition of further acid to individual reaction regions.

In one embodiment, the liquid output stream of one reaction region is passed to a subsequent reaction region with the aid of a pump. In further embodiments, the discharge is also introduced into a subsequent reaction region with the aid of an overflow or is passed into the lower part of the rectification column, from where the rectification mixture, freed from low boilers, flows into the reaction region which has a liquid connection to the rectification column.

In an advantageous embodiment of the invention, the content of catalytically active acid in the first reaction region is from 0.1 to 5% by weight, based on the reaction mixture contained therein, of sulfuric acid (or an equimolar amount of an organic sulfonic acid, preferably methanesulfonic acid, benzenesulfonic acid, dodecylbenzenesulfonic acid or p-toluenesulfonic acid or of a mixture of an organic sulfonic acid and sulfuric acid). The corresponding acid content in the last reaction region is preferably from >5 to 20% by weight. The total residence time of the reactants in the cascade is as a rule from 1 to 20 hours.

Where the individual reaction regions are reactors which are spatially separated from one another, the number thereof is advantageously >2 and ≦4, taking into account the capital costs. If more than one reaction region is created within one and the same reactor (for example by using partitions), the number of reaction regions may also be greater than 4.

Figure 1:
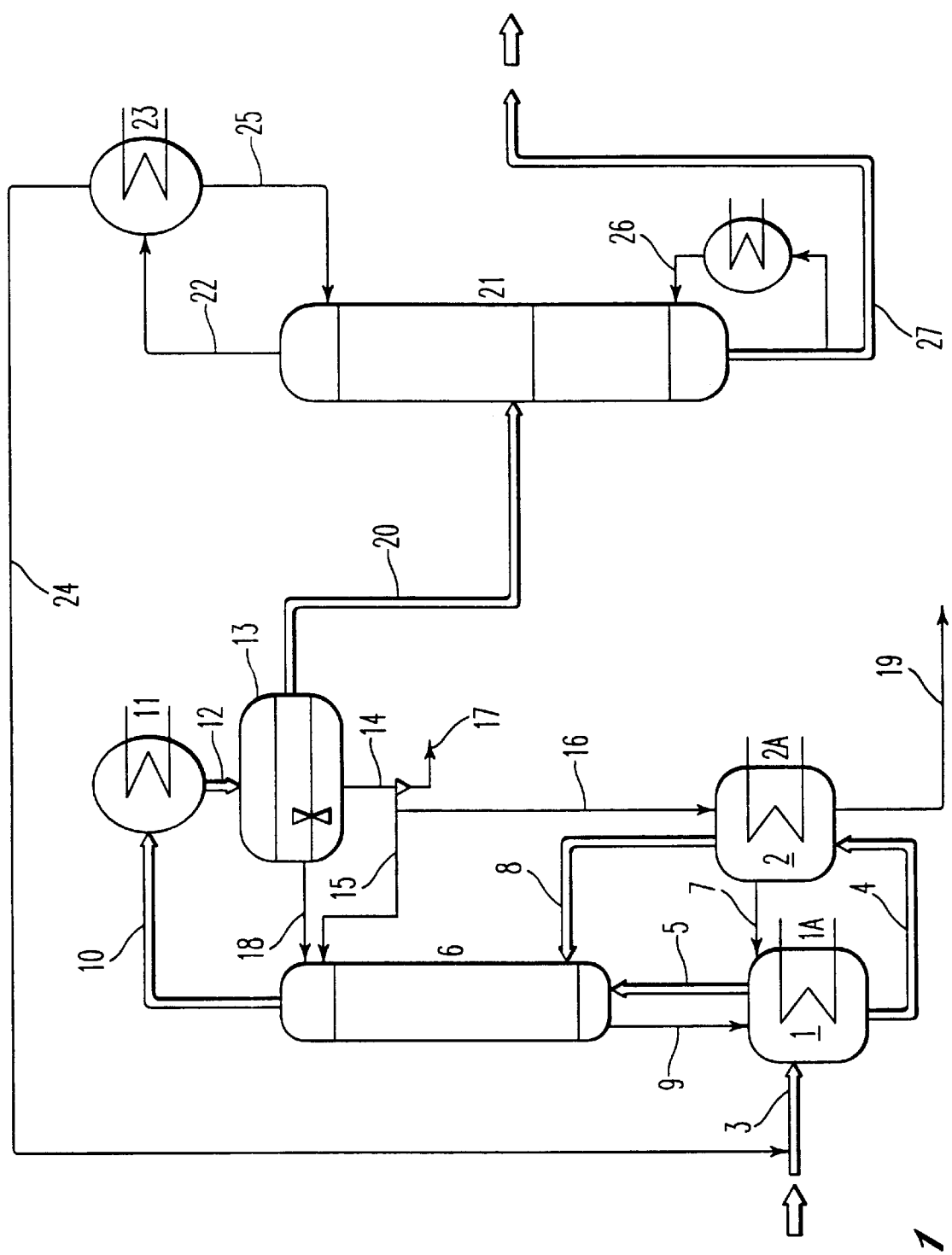
FIG. 1 is a schematic view of an apparatus for carrying out the process of the invention.

In a possible embodiment of the novel process, only one rectification column is mounted on the total reaction zone, the liquid reflux of said column being connected only to the first reaction region. With regard to the remaining reaction regions, there is a connection to the rectification column only for the ascending vapors. In a further embodiment, the first reaction region is operated as a dwell container (preliminary reactor) without a connection to the rectification column. Preferably the first reaction region is connected on the gas side neither to a downstream reaction region nor to the rectification zone. The top pressure of the rectification column is advantageously from 0.1 to 1 atm, atmospheric pressure being particularly preferred.

The temperature of the reaction mixture in the various reaction regions usually corresponds to the boiling point of the particular reaction mixture at the set pressure, ie. it usually increases along the cascade, which is advantageous with regard to the objects of the process. In the first reaction region, the temperature is usually $\geq 80°$ C. and $\leq 125°$ C. In the last reaction region of the cascade, it should be $\leq 135°$ C., in order to suppress undesirable polymerization as a secondary reaction.

The conversions are typically $\geq 95$ mol %, based on the amount of (meth)acrylic acid used. The first reaction region is advantageously operated at a conversion as high as $\geq 90$ mol %. When a dwell reactor (preliminary reactor) is used as the first reaction region, the reaction mixture therein generally does not boil. Here too, the recommended reaction temperature is from 80° to 125° C. When a dwell reactor is used as the first reaction region, a conversion of about 80% of the equilibrium value is reached as a rule. Advantageously, the reaction regions are designed so that the residence time decreases along the cascade from reaction region to reaction region.

In an advantageous embodiment of the invention, the molar alkanol/(meth)acrylic acid ratio used is $\geq 1$ and is as a rule less than 5. A ratio of from 1:1 to 3:1 is particularly advantageous. A ratio of from 1.1:1 to 1.8:1 is very particularly advantageous. It is particularly advantageous to use sulfuric acid and/or organic sulfonic acids as esterification catalysts.

As a rule, it is sufficient continuously to remove $\leq 2.5\%$ by weight, based on the amount of ester obtained, of reaction mixture from the reaction zone, preferably from the last reaction region, in order to limit the amount of high-boiling non-cleavable byproducts.

Advantageously, a part-stream is recycled from the last reaction region of the cascade to the first reaction region and, if required, to other reaction regions. Acidic esterification catalyst is removed together with the high boilers and is continuously added to the reaction mixture. Process stabilizer is also simultaneously removed, so that its content settles to a steady-state value. This leads to steady-state conditions of the required concentration of acidic esterification catalyst. At the same time, this circulation dispenses with working up of the catalyst and reduces the requirement for fresh catalyst.

Since the acrylic acid used contains small amounts of acetic acid, alkyl esters of acetic acid are obtained as byproducts, in addition to dialkyl ethers. Both secondary components pass over via the top of the attached rectification column and, in the alkanol/ester separation by distillation, remain in the alkanol, which is advantageously recycled to the starting mixture. As a result, both impurities accumulate in the return streams. Steadystate concentrations are established by virtue of the fact that, to a certain extent, these low boilers enter the resulting ester. Depending on purity requirements for the ester, removal from the alkanol circulation too is therefore effected.

In a simple distillation column downstream of the alkanol/ester separation, the ester can be separated from the process stabilizers by distillation and can be treated with storage stabilizers in their place. Preferably the acid to be esterified is acrylic acid and/or the alkanol to be esterified is a $C_1$–$C_4$-alkanol, especially n-butanol.

The novel process is particularly preferably used for the preparation of n-butyl acrylate.

The vapors formed in the reaction zone set up according to the invention as a cascade are fed continuously to a rectification zone, as described above. With regard to the aqueous azeotropic mixture separated therefrom via the top and containing the target ester, it is possible to make a distinction essentially between two cases. If it is a hetero azeotropic mixture, as, for example, in the case of the preparation of n-butyl acrylate, the azeotropic mixture separates after its condensation spontaneously into an aqueous phase and into an organic phase. The aqueous phase usually consists mainly of water and a little alkanol, while the organic phase generally consists essentially of the resulting ester and alkanol. In order to establish the rectificative separation effect, an appropriate part of the organic phase is recycled via the top of the rectification zone.

In order to maintain the composition of the aqueous azeotropic mixture, an appropriate part of the aqueous phase is recycled to the reaction zone, preferably likewise via the top of the attached rectification zone. Alkanol present can be separated from the unrecycled part of the aqueous phase, for example by stripping (for example with air) and is recycled to the reaction zone. Recycling is advantageously effected directly. The resulting essentially pure water is discharged. The alkyl (meth)acrylate formed is separated in a manner known per se, for example according to DE-A 25 52 987, from the unrecycled part of the organic phase. For example, the excess organic phase is fed to a downstream rectification column and the alkanol is separated off via the top in pure form or as an azeotropic mixture consisting of ester and alkanol. The alkanol thus separated off (in pure or in azeotropic form) is preferably recycled to the reaction zone. Recycling is advantageously effected directly.

The bottom liquid of this rectification column consists essentially of the desired ester and small amounts of byproducts having lower and higher boiling points than this ester. The bottom liquid of this rectification column is therefore also referred to as crude alkyl (meth)acrylate. The lower-boiling byproducts are in particular the dialkyl ether and the acetate of the starting alkanol, since the esterification of (meth)acrylic acid with alkanols usually takes place starting from crude (meth)acrylic acid. This is produced predominantly by catalytic gas-phase oxidation of $C_3/C_4$ starting compounds, such as propene or isobutene, minor amounts of acetic acid being formed as a byproduct (cf. for example DE-A 44 36 243). Highers boiling byproducts are, for example, oligo- and polymers of the $\alpha,\beta$-monoethylenically unsaturated target ester.

In a downstream low-boiler rectification column, the lower-boiling byproducts are separated off from the crude alkyl (meth)acrylate, usually via the top, before the desired pure alkyl (meth)acrylate can be separated off via the top in a high-boiler rectification column downstream from this. The bottom liquid of the high-boiler rectification column, which liquid contains the higher-boiling byproducts, is advantageously recycled to the reaction zone, preferably directly.

In a particular embodiment, if acetate is separated off from the return butanol stream, which is effected as described above, the ester is removed from the rectification column for recovery of butanol by a side take-off after separation of any entrained liquid droplets and is condensed to give pure ester. In the condensation, the storage stabilizer is added to this (eg. hydroquinone monomethyl ether). In this embodiment, the bottom discharge of the rectification column for butanol recovery (mainly comprising alkyl acrylate) is advantageously recycled to the last reaction region of the cascade for cleavage of small amounts of high boilers present and for recovery of pure ester.

In both cases, a small amount of reaction mixture is discharged, preferably continuously, from this last reaction region of the cascade in order to maintain a steady state and to avoid accumulation of high boilers there. The amount of acid catalyst simultaneously discharged is added to the reaction zone.

Usually, the aqueous azeotropic mixture removed from the reaction zone contains no starting acid when the rectificative separation action is correctly established. However, if the latter is not the case, said acid can be separated off together with the alkanol by extraction with water and the extract then separated in a manner known per se by rectification. In the novel process, both the esterification reaction and the rectificative separations and extractions are preferably carried out in the presence of conventional amounts of conventional polymerization inhibitors. As a rule, from 0.01 to 0.1% by weight, based on the amount of the $\alpha,\beta$-monoethylenically unsaturated monomers, of a suitable polymerization inhibitor is used. They are advantageously added at the top of the attached rectification column and at the top of the alkanol/ester separation column. Examples of suitable polymerization inhibitors are phenolic compounds, such as hydroquinone and hydroquinone monomethyl ether, as well as p-benzoquinone, phenothiazine, methylene blue, phenylenediamine and/or air.

Compared with the prior art processes, the novel process is distinguished by a substantial reduction in the number of steps and separation operations, shorter residence times, a higher yield of desired ester, based on starting acid used, a smaller amount of ether and a reduced discharge of the liquid phase from the reaction zone and by the fact that it is no longer necessary to work up this discharge from the reaction zone. Both the latter and the increased yield are probably due to the fact that the steady state established in the reaction zone is kinetically controlled. The recleavage of relatively high-boiling oxyesters (for example alkoxypropionates or acyloxypropionates) probably plays a key role.

In an advantageous embodiment, the total process is operated with a total of four separation columns for removing high boilers and low boilers. These are the column for removing the ester via the top, the butanol recovery column, the acetate column for removing acetates from the return butanol stream and a stripping column for removing residual butanol from the removed water of reaction.

BRIEF DESCRIPTION OF THE DRAWINGS

The invention also relates to an apparatus for carrying out the described process for the continuous preparation of alkyl esters of (meth)acrylic acid, having a first reactor (1) which is provided with a feed line (3) for the reactants and whose top is connected via a line (5) to the lower part of a rectification column (6) whose top is connected via a condenser to a separator (13) which has a discharge line (20) for the crude product, wherein the lower end of the first reactor (1) is connected via a line (4) to the lower end of at least one further reactor (2) whose top is connected via a line (8) to the lower part of the rectification column (6).

Preferably the upper part of at least one further reactor (2) is connected via a line (7) to the upper part of the first reactor (1).

Preferably the lower part of the rectification column (6) is connected via a line (9) to the top part of the first reactor (1).

Preferably the lower part of the separator (13) is connected to the top part of the rectification column (6) and to the top part of at least one of the further reactors (2).

Preferably the separator (13) is connected to a further rectification column (21).

The invention also relates to an apparatus for carrying out the described process for the continuous preparation of alkyl esters of (meth)acrylic acid, having a reactor (1) which is provided with a feed line (3) for the reactants and which, as a dwell container, forms the first reaction region, wherein the first reactor (1) has a liquid-side connection (4) to at least one further reactor (2) whose top is connected via a line (8) to the lower part of the rectification column (6) whose top is connected via a condenser to a separator (13) which has a discharge line (20) for the crude product.

Preferably at least one of the further reactors (2) has a connecting line (7) to the first reactor (1).

Preferably the lower part of the rectification column (6) is connected via a line (9) to the top part of one of the further reactors (2).

Preferably the lower part of the separator (13) is connected to the top part of the rectification column (6) and to one of the further reactors (2).

Preferably the separator (13) is connected to a further rectification column (21).

Further details and advantages of the invention are evident from the Examples described with reference to the drawing. It should be emphasized once again at this point that all statements above and below are valid in particular for the process for the preparation of n-butyl acrylate, ie. butanol is n-butanol.

EXAMPLE 1

This Example is to be described below with reference to FIG. 1. Here, a mixture of 5 mol/h of acrylic acid (AA) and 7 mol/h of butano (BuOH) and sulfric acid as an esterification catalyst was fed, via a feed line 3, to a reactor 1 having a forced-circulation evaporator 1A. The amount of sulfuric acid was from 2 to 3% by weight, based on the reaction mixture. The reaction was carried out at 120° C. and 1 atm and during a residence time of 2.5 h. The gaseous reaction product was fed from the top of reactor 1 via a line 5 to a rectification column. A part-stream of the reaction mixture (stream 4) was pumped continuously by means of a circulation pump (not shown) from the lower part of reactor 1 into the lower part of a second reactor 2 having a forced-circulation evaporator 2A. The second reactor was operated at the higher temperature of 130° C. and at a higher sulfuric acid concentration of about 10% by weight. Reactor 2 had an overflow 7 to reactor 1, by means of which a constant catalyst concentration was maintained in reactor 1. Reactor 2 likewise had a gas-side connection 8 to the lower part of distillation column 6. Its liquid outflow was passed via a line 9 into reactor 1. The subsequent reaction and the in situ cleavage of oxy compounds (Michael adducts) formed took place in reactor 2. The two reactors 1 and 2 connected to one another at their lower end via line 4 formed the novel reaction zone built up as a cascade. The gas flowing continuously from this reaction zone into distillation column 6 was rectified there, and the aqueous azeotropic mixture flowing away from the top of this distillation column 6 via line 10, containing the target ester to be formed and consisting of butyl acrylate, butanol and water was fed to a condenser 11 and condensed therein. The condensate flowed via a line 12 into a separator 13. There, the azeotropic mixture separated into an aqueous phase and into an organic phase. The aqueous phase, which comprised mainly water and a little butanol, was taken off through line 14 and fed partially via line 15 to the top of distillation column 6 to effect the rectificative separation as well as azeotrope formation of the vapors ascending there. Another part of the aqueous phase was fed via line 16 to the top of reactor 2. A further part was removed via line 17 for stripping off butanol. In the experimental setup, half the amount of reflux flowing away through line 14 from the condenser was fed via line 15 into the distillation column and half via line 16 into reactor 2. Organic reflux was fed from separator 13 via line 18 into the top of distillation column 6 in order to suppress the acrylic acid. The aqueous reflux was effected under temperature regulation and the organic reflux under level control. The line 19 provided on the lower part of reactor 2 served for disposal of remaining residues.

The organic phase consisting essentially of butanol and butyl acrylate contained only 876 ppm (ppm data are all based on weight) of dibutyl ether. It was removed continuously from separator 13 via a line 20 and introduced as feed to a further column 21 which was in the form of a bubble-cap column in the experimental setup, in order to recover butanol. In this butanol recovery column 21, the excess butanol, with residues of water and portions of butyl acrylate, was removed via the top through line 22 and fed to a condenser 23. From the latter, the excess butanol was added via line 24 to the mixture of reactants which was introduced into reactor 1 through line 3. A part of the distillate was fed from separator 23 via line 25 to the top of column 21 as a reflux for increasing the rectificative separation.

Crude butyl acrylate which was free of high boilers, contained only residues of low boilers and had a butyl acrylate content of 99.5% by weight was removed from the bottom of butanol recovery column 21 via a line 27. After subsequent removal of low boilers and high boilers, it was possible to obtain a pure butyl acrylate having a purity of >99.9% by weight. Butanol recovery column 21 was operated at 400 mbar. The pure ester contained only 598 ppm of dibutyl ether. A temperature of 115° C. was established in the bottom of this column by means of heat exchanger 26.

A second experiment under the same conditions with only a reduced butanol excess (molar ratio 1.3:1) resulted in a decrease of the ether in stream 20 to 623 ppm and an increase of 374 ppm in the amount of pure product. The yield of butyl acrylate, based on acrylic acid, was 98.8% of theory in the first experiment and 97.3% of theory in the second experiment.

COMPARATIVE EXAMPLE

For comparison, a known esterification process was carried out using only one reaction region. In this Comparative Example, 4 mol/h of acrylic acid, 4 mol/h of fresh butanol and 1.6 mol/h of recycled butanol (distillate from the butanol recovery) were fed to a circulation evaporator (2.5 l, level of fill 2 l). The residence time was 2.5 h. The esterification was carried out in the presence of 9.7% by weight (based on the reaction mixture) of sulfuric acid at 126° C. The reactor was connected to a bubble-cap column (30 trays), which was stabilized with 15 ml/h of hydroquinone monomethyl ether (MeHQ) in butanol. Butyl acrylate formed was removed via the top by adding 340 ml/h of water as a reflux (azeotropic entraining agent) to the column. In addition, 175 ml/h of organic reflux were added to the column in order to suppress the acrylic acid.

The excess organic phase (610 ml/h) was added continuously as a feed to a second bubble-cap column, as in the Example for the novel process for the recovery of butanol (BuOH). A crude ester containing 1295 ppm of dibutyl ether was obtained in the bottom of the butanol column, which was at 115° C. 1940 ppm of ether were present in the feed to the BuOH column. The column was stabilized with MeHQ (2% by weight in butanol).

After removal of the low boilers and high boilers, a pure ester having a purity of >99.9% by weight was obtained. The yield was 98.4% of theory, based on acrylic acid.

EXAMPLE 2

Figure 2:
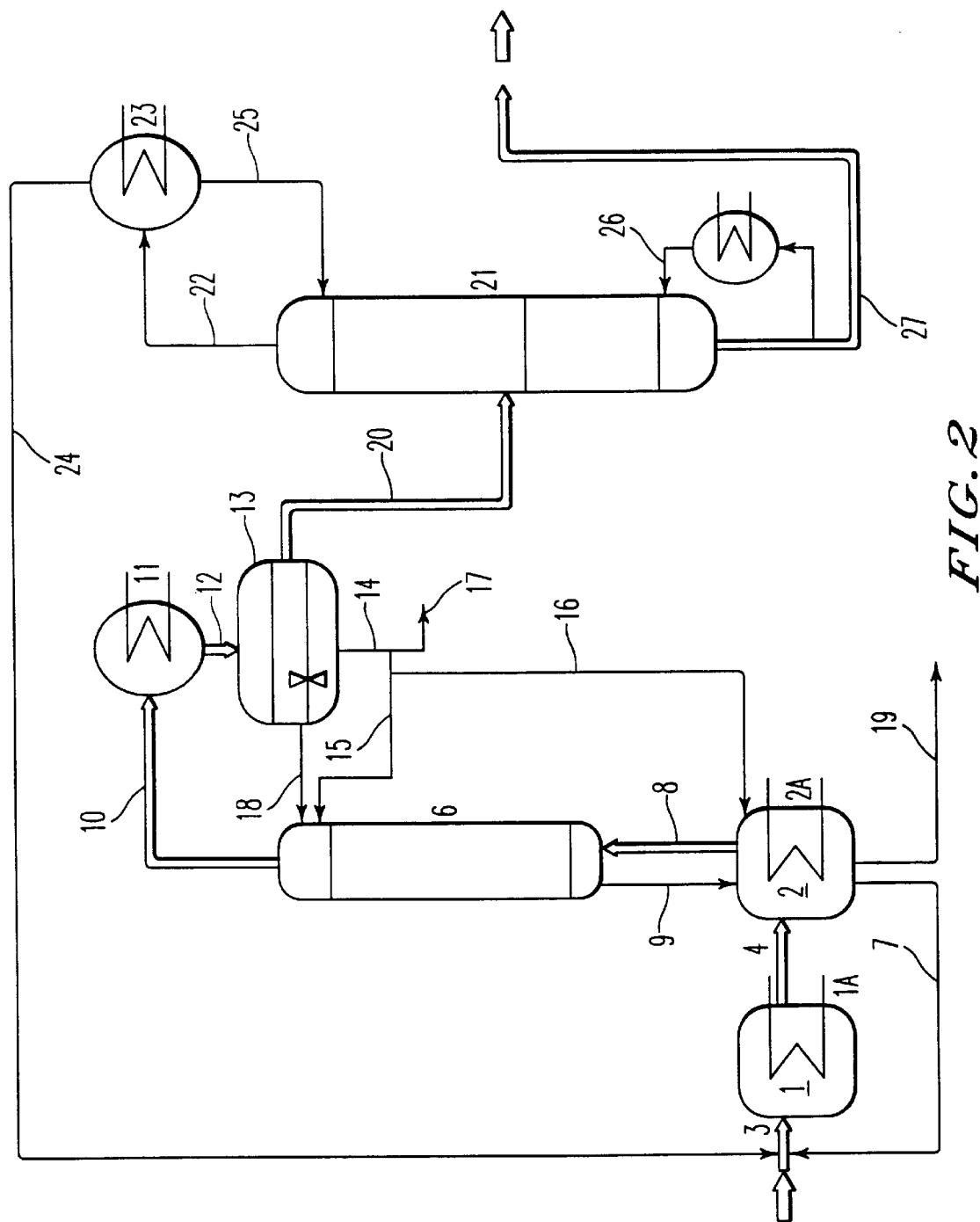
FIG. 2 is a schematic view of a preferred embodiment of the apparatus.

This Example is to be described with reference to FIG. 2. Here, the same reference symbols as in FIG. 1 were used for identical or corresponding parts.

A mixture of 5 mol/h of acrylic acid (AA) and 5.5 mol/h of n-butanol (BuOH) and sulfuric acid as an esterification catalyst was fed via a feed line 3 to a reactor (dwell reactor) 1 having a forced-circulation evaporator 1A. The molar BuOH/AA ratio was 1.1:1. The amount of sulfuric acid was from 2 to 3% by weight (based on the reaction mixture). The reaction in reactor 1 was carried out at 120° C. and during a residence time of 3.5 h. A part-stream of liquid reaction mixture was passed continuously from reactor 1 via line 4 to the second reactor 2. This second reactor was operated at the higher temperature of 130° C. and at a higher sulfuric acid concentration of about 10% by weight. Reactor 2 had a liquid recycle 7 to reactor 1, by means of which recycle a constant catalyst concentration was maintained in reactor 1. Reactor 2 had a gas-side connection 8 to the lower part of distillation column 6. Its liquid outflow was passed via a line 9 to reactor 2. The subsequent reaction and the in situ cleavage of oxy compounds (Michael adducts) formed took place in reactor 2. The two reactors 1 and 2 connected to one another by line 4 formed the novel reaction zone built up as a cascade.

The reaction mixture was worked up similarly to the isolation of pure ester, described in the first Example. The crude ester removed at the lower end of butanol recovery column 21 contained 134 ppm of dibutyl ether before removal of low boilers and high boilers. The pure ester contained 99.9% by weight of butyl acrylate. The yield of butyl acrylate was 98.1% of theory (based on acrylic acid).

We claim:

1. A process for the continuous preparation of alkyl esters of (meth)acrylic acid by reacting (meth)acrylic acid and a monohydric alkanol of 1 to 8 carbon atoms in the homogeneous, liquid, solvent-free phase at elevated temperatures and in the presence of an acidic esterification catalyst, in which the (meth)acrylic acid, the alkanol and the acid catalyst are fed continuously to a reaction zone, the alkyl (meth)acrylate formed is separated off by rectification, after a residence time, via the top of a rectification zone mounted on the reaction zone, as a component of at least one azeotropic mixture consisting of water or water and starting alkanol as further components in addition to the alkyl (meth)acrylate, the resulting distillate is separated into at least one organic phase containing the alkyl (meth)acrylate and into at least one water-containing aqueous phase, a part of the organic phase containing alkyl (meth)acrylate is recycled via the top of the rectification zone and, if required, water is recycled to the reaction zone, the alkyl (meth) acrylate is isolated from the excess organic phase containing the alkyl (meth)acrylate and a part of the reaction mixture is discharged continuously from the reaction zone, wherein the reaction zone consists of a cascade of at least two reaction regions, connected in series, and the discharge stream of one reaction region forms a feed stream of a subsequent reaction region and the amount by weight, based on the amount of esterification mixture contained in the particular reaction region, of the acidic esterification catalyst increases along the reaction cascade.

2. A process as claimed in claim 1, wherein the cascade has from two to four reaction regions spatially separated from one another.

3. A process as claimed in claim 1, wherein the ascending vapors from the reaction regions are fed to an individual rectification zone whose liquid reflux is recycled only to the first reaction region.

4. A process as claimed in claim 1, wherein the first reaction region is connected on the gas side neither to a downstream reaction region nor to the rectification zone.

5. A process as claimed in claim 1, wherein the temperature in the first reaction region is from 80° to 125° C. and that in the last reaction region is higher than that in said first reaction region and below 135° C.

6. A process as claimed in claim 1, wherein the top pressure of the rectification column is from 0.1 to 1, preferably 1, atm, and/or wherein the total residence time of the reactants in the cascade is from 1 to 20 hours.

7. A process as claimed in claim 1, wherein the molar alkanol/(meth)acrylic acid ratio used is $\geq 1$, preferably wherein the molar ratio used and fed to the first reaction region is from 1:1 to 3:1, preferably from 1:1 to 1.8:1.

8. A process as claimed in claim 1, wherein sulfuric acid or an organic sulfonic acid, preferably methanesulfonic acid, benzenesulfonic acid, dodecylbenzenesulfonic acid or p-toluenesulfonic acid is used as the esterification catalyst.

9. A process as claimed in claim 1, wherein the content of catalytically active acid in the first reaction region is from 0.1 to 5% by weight, based on the reaction mixture contained therein, of sulfuric acid or an equimolar amount of organic sulfonic acid.

10. A process as claimed in claim 1, wherein the content of catalytically active acid in the last reaction zone is from 5 to 20% by weight, based on the reaction mixture contained therein, of sulfuric acid or an equimolar amount of organic sulfonic acid.

11. A process as set forth in claim 5 wherein the residence time of the esterification mixture in said last reaction region is less than the residence time of the esterification mixture reactants in said first reaction region.

12. A process as claimed in claim 1 wherein the increase in acidic esterification catalyst along the reaction cascade is achieved by external addition of further acid to individual reaction regions.

13. A process as claimed in claim 1 wherein said monohydric alkanol has 1 to 4 carbon atoms.

14. A process as set forth in claim 1 wherein said monohydric alkanol is butyl alcohol.

15. A process as set forth in claim 1 wherein the catalyst concentration of the first reaction region of said cascade is from 2 to 3% by weight and the catalyst concentration in the last reaction region of said cascade is about 10% by weight.

16. The process of claim 15 wherein the monohydric alkanol used to esterify said (meth)acrylic acid is butyl alcohol.

* * * * *